United States Patent [19]

Kolattukudy et al.

[11] Patent Number: 5,512,203
[45] Date of Patent: Apr. 30, 1996

[54] CUTINASE CLEANING COMPOSITIONS

[75] Inventors: Pappachan Kolattukudy, Columbus, Ohio; Ayrookaran J. Poulose, Belmont, Calif.

[73] Assignee: Genencor International, Inc., Rochester, N.Y.

[21] Appl. No.: 283,879

[22] Filed: Aug. 1, 1994

Related U.S. Application Data

[63] Continuation of Ser. No. 800,365, Nov. 27, 1991, abandoned, which is a continuation-in-part of Ser. No. 600,836, Oct. 22, 1990, abandoned, which is a continuation of Ser. No. 341,200, Mar. 29, 1989, Pat. No. 4,981,611, which is a continuation of Ser. No. 56,500, May 29, 1987, abandoned.

[51] Int. Cl.$^6$ .................................................. C11D 3/386
[52] U.S. Cl. ........................... 252/174.12; 257/DIG. 12; 257/95; 257/99; 252/550; 252/551; 252/174.21; 134/42
[58] Field of Search ...................... 252/174.12, DIG. 12, 252/95, 99, 550–551, 174.21; 134/42; 435/198

[56] References Cited

U.S. PATENT DOCUMENTS

| | | | |
|---|---|---|---|
| 3,704,228 | 11/1972 | Eckert et al. | 252/112 |
| 3,950,277 | 4/1976 | Stewart et al. | 252/541 |
| 4,011,169 | 3/1977 | Diehl et al. | 252/95 |
| 4,981,611 | 1/1991 | Kolattukudy | 252/550 |
| 5,030,240 | 7/1991 | Wiersema et al. | 8/111 |
| 5,108,457 | 4/1992 | Poulose | 8/111 |

FOREIGN PATENT DOCUMENTS

| | | |
|---|---|---|
| 0399681 | 11/1990 | European Pat. Off. . |
| WO94/03578 | 2/1994 | WIPO . |

OTHER PUBLICATIONS

Sebastien et al, "Discovery of Cutinase–Producing Pseudomonas sp. Cohabiting with an Apparently Nitrogen––Fixing Coryebacterium sp. in the Phyllosphere," Journal of Bacteriology, Jan. 1987, vol. 169, No. 1, pp. 131–136.

Kolattukudy, P. E. "Cutinases from Fungi and Pollen", *Lipases*, Borgstrom & Brockman (Ed.) Elsevier Publ. Amsterdam, pp. 471–504, 1984.

*Primary Examiner*—Paul Lieberman
*Assistant Examiner*—Kery A. Fries
*Attorney, Agent, or Firm*—Margaret A. Horn

[57] ABSTRACT

Disclosed herein are cleaning compositions and methods for using them. In particular, disclosed herein are cleaning compositions comprising a cutinase enzyme and a cutinase compatible surfactant.

16 Claims, 1 Drawing Sheet

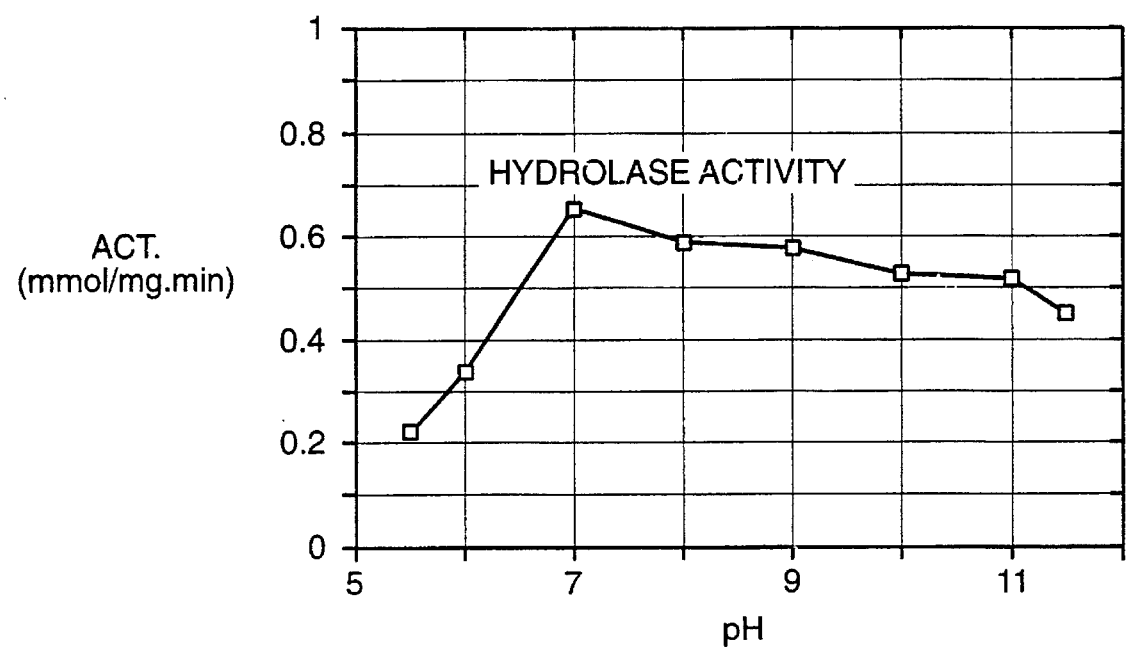
FIG._1
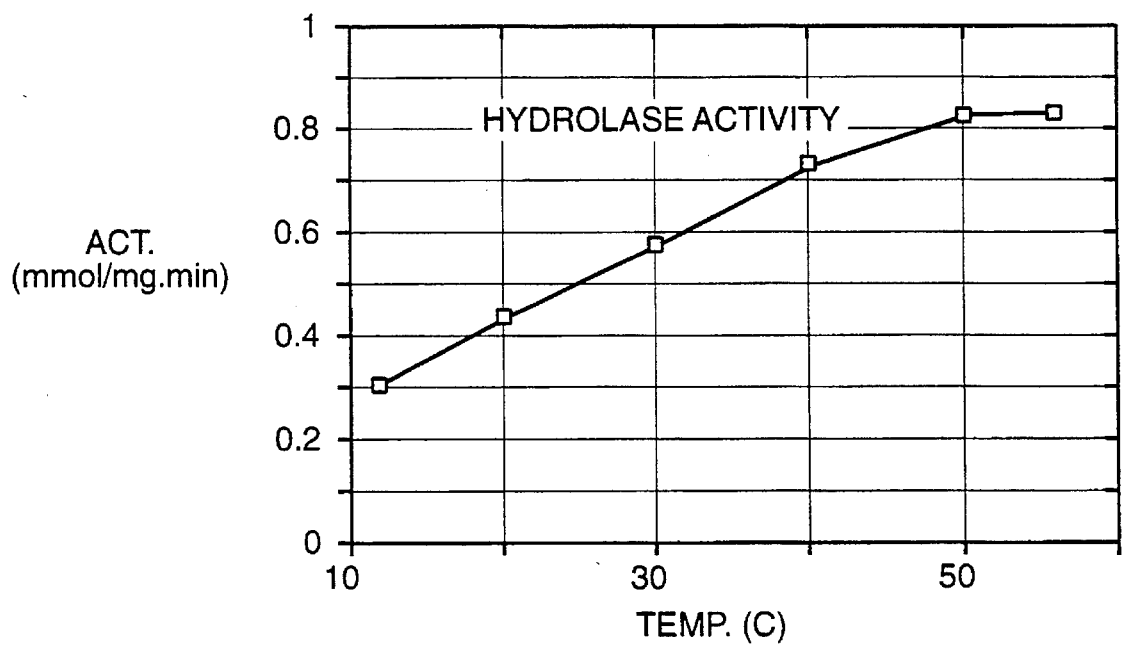
FIG. 2

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 258 amino acids
        ( B ) TYPE: amino acid
        ( D ) TOPOLOGY: linear ( i i ) MOLECULE TYPE: protein ( i i i ) HYPOTHETICAL: NO ( i v ) ANTI-SENSE: NO ( v i ) ORIGINAL SOURCE:
        ( A ) ORGANISM: Pseudomonas mendocina
        ( C ) INDIVIDUAL ISOLATE: ATCC 53552

( x i ) SEQUENCE DESCRIPTION: SEQ ID NO:1:

```
Ala  Pro  Leu  Pro  Asp  Thr  Pro  Gly  Ala  Pro  Phe  Pro  Ala  Val  Ala  Asn
 1                  5                        10                      15

Phe  Asp  Arg  Ser  Gly  Pro  Tyr  Thr  Thr  Ser  Ser  Gln  Ser  Glu  Gly  Pro
             20                       25                      30

Ser  Cys  Arg  Ile  Tyr  Arg  Pro  Arg  Asn  Leu  Gly  Gln  Gly  Gly  Val  Arg
             35                       40                      45

His  Pro  Val  Ile  Leu  Trp  Gly  Asn  Gly  Thr  Gly  Ala  Gly  Pro  Ser  Thr
      50                       55                      60

Tyr  Ala  Gly  Leu  Leu  Ser  His  Trp  Ala  Ser  His  Gly  Phe  Val  Val  Ala
 65                       70                      75                      80

Ala  Ala  Glu  Thr  Ser  Asn  Ala  Gly  Thr  Gly  Arg  Glu  Met  Leu  Ala  Cys
                   85                       90                      95

Leu  Asp  Tyr  Leu  Val  Arg  Glu  Asn  Asp  Thr  Pro  Tyr  Gly  Thr  Tyr  Ser
             100                      105                     110

Gly  Lys  Leu  Asn  Thr  Gly  Arg  Val  Gly  Thr  Ser  Gly  His  Ser  Gln  Gly
             115                      120                     125

Gly  Gly  Gly  Ser  Ile  Met  Ala  Gly  Gln  Asp  Thr  Arg  Val  Arg  Thr  Thr
```

```
                        130                         135                             140

Ala  Pro  Ile  Gln  Pro  Tyr  Thr  Leu  Gly  Leu  Gly  His  Asp  Ser  Ala  Ser
145                      150                      155                           160

Gln  Arg  Arg  Gln  Gln  Gly  Pro  Met  Phe  Leu  Met  Ser  Gly  Gly  Gly  Asp
                    165                      170                           175

Thr  Ile  Ala  Phe  Pro  Tyr  Leu  Asn  Ala  Gln  Pro  Val  Tyr  Arg  Arg  Ala
               180                      185                         190

Asn  Val  Pro  Val  Phe  Trp  Gly  Glu  Arg  Arg  Tyr  Val  Ser  His  Phe  Glu
          195                      200                         205

Pro  Val  Gly  Ser  Gly  Gly  Ala  Tyr  Arg  Gly  Pro  Ser  Thr  Ala  Trp  Phe
     210                      215                      220

Arg  Phe  Gln  Leu  Met  Asp  Asp  Gln  Asp  Ala  Arg  Ala  Thr  Phe  Tyr  Gly
225                      230                      235                           240

Ala  Gln  Cys  Ser  Leu  Cys  Thr  Ser  Leu  Leu  Trp  Ser  Val  Glu  Arg  Arg
               245                      250                         255

Gly  Leu
```

( 2 ) INFORMATION FOR SEQ ID NO:2:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:2:

CCAACTGTCGC  TGCAGGAAAA  GCTCCCCTGC                        30

( 2 ) INFORMATION FOR SEQ ID NO:3:

( i ) SEQUENCE CHARACTERISTICS:
        ( A ) LENGTH: 20 base parrs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:3:

GCAGGCTGCA  GGAAAAAGCA                        20

( 2 ) INFORMATION FOR SEQ ID NO:4:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) SEQUENCE DESCRIPTION: SEQ ID NO:4:

TGCGCAGGCT  GCTCCCCTGC                        20

CUTINASE CLEANING COMPOSITIONS

CROSS-REFERENCE TO RELATED APPLICATIONS

This application is a continuation of U.S. application No. 07/800,365, filed Nov. 27, 1991 now abandoned which is a continuation-in-part of U.S. patent application Ser. No. 07/600,836, filed Oct. 22, 1990, now abandoned, which is a continuation of U.S. patent application Ser. No. 07/341,200, filed Mar. 29, 1989, now U.S. Pat. No. 4,981,611, which, in turn, is a continuation from U.S. patent application Ser. No. 07/056,500, filed May 29, 1987 and which is now abandoned. PCT application Ser. No. PCT/US88/01844 filed May 31, 1988 claims priority from U.S. patent application No. 07/056,500 filed May 29, 1987 and which is now abandoned. Each of the above applications are incorporated herein by reference in their entirety.

BACKGROUND OF THE INVENTION

1. Field of the Invention

This invention relates to enzymatic surfactant cleaning compositions and to methods of using such compositions. Specifically, this invention relates to surfactant cleaning compositions comprising a cutinase enzyme and a cleaning effective amount of a compatible surfactant as well as to methods for enzymatically cleaning a material having a cutin or cutin-like stain by using such compositions.

2. State of the Art

A wide variety of enzymes are well known for use in cleaning compositions. The use of *B. subtilisins* and *B. licheniformis* protease in commercial preparations is common. Likewise, other enzymes have been proposed for use in commercial cleaning compositions. For example, the use of lipases in cleaning compositions is disclosed in U.S. Pat. No. 4,011,169, and British Patent No. 1,293,613. Also, a comprehensive review article of lipases in cleaning compositions can be found in the *Journal of Applied Biochemistry*, Vol. 2, pp 218–229 (1980) in an article entitled "Lipases as Detergent Components." Lipolytic detergent additives are also known from, e.g., British Patent Specification No. 1,293,613 and Canadian Patent No. 835,343.

Similarly, U.S. Pat. No. 3,950,277 and British Patent Specification No. 1,442,418 disclose lipase enzymes combined with an activator and calcium and/or magnesium ions, respectively, which are utilized to pre-soak soiled fabrics and to remove triglyceride stains and soils from polyester or polyester/cotton fabric blends, respectively. Suitable microbial lipases for use therein (apart from animal and plant derived lipases) are said to be those derived from Pseudomonas, Aspergillus, Pneumococcus, Staphylococcus and Staphylococcus toxins, *Mycobacterium tuberculosis, Mycotorula lipolytica*, and Sclerotinia.

British Patent Specification No. 1,372,034 discloses a cleaning composition comprising a bacterial lipase produced by *Pseudomonas stutzeri* strain ATCC 19154. Furthermore, this reference discloses that the preferred lipolytic enzymes should have a pH optimum between 6 and 10, and should be active in said range, preferably between 7 and 9. Around 1970, this presumed *Pseudomonas stutzeri* strain was reclassified as *Pseudomonas aeruginosa*, as evidenced by the ATCC catalogs.

European Patent Application No. 0 130 064 discloses an enzymatic detergent additive comprising a lipase isolated from *Fusarium oxysporum* with an alleged higher lipolytic cleaning efficiency than conventional lipases.

European Patent Application No. 0 214 761 discloses enzymatic detergent additives including a microbially produced lipase from the strain of *Pseudomonas cepacia*. The lipases described therein are claimed to be superior to the lipolytic detergent action of prior art lipases, especially at low temperature washing processes (around 60° C. and below).

PCT Patent Application No. WO 87/00859 discloses other novel lipolytic enzymes which are described as having an optimal pH in the range of 8–10.5 at a temperature of 60° C. or less. These lipases are produced from bacterial strains selected from the group consisting of *Pseudomonas pseudoalcaligenes, P. stutzeri* and *Acinetobacter calcoaceticus*. These enzymes are described as particularly effective at low temperatures, i.e., 40° C. or lower and effective in both liquid and solid detergent compositions.

While the above-cited references disclose the use of lipases in cleaning compositions, these references do not disclose the use in cleaning compositions of cutinase enzymes derived from any microbial source let alone cutinase enzymes derived from Pseudomonas. Moreover, while the above-cited references suggest use of lipases in cleaning compositions, commercial use of lipases in such compositions has been impeded by virtue of the fact that a majority of lipases have one or more properties that are incompatible with the cleaning composition. For example, some lipases possess pH optima in the acidic range whereas most cleaning compositions require a neutral or alkaline medium in order to effectively clean. Additionally, some lipases are not oxidatively stable in the presence of oxidants such as bleaches commonly formulated into commercial cleaning compositions and/or are not stable in the presence of protease enzymes also commonly formulated into commercial cleaning compositions. Moreover, lipases, while effective on many lipids, are not completely effective against all lipid stains commonly found in laundry and other cleaning applications. Thus, while lipases possess enzymatic properties beneficial to cleaning such as the ability to hydrolyze oily stains (e.g., triglyceride stains on garments), the above-noted problems have impeded the universal use of lipases in commercial cleaning compositions.

In view of the above, it would be particularly advantageous to incorporate an enzyme into such cleaning compositions wherein the enzyme was capable of cleaning common stains such as oily stains cutin-like stains, and/or cutin stains. It would also be particularly advantageous if the enzyme was active under neutral or alkaline conditions and was stable under oxidative conditions, and was stable in the presence of other enzymes such as proteases.

SUMMARY OF THE INVENTION

The present invention is directed to the discovery that microbial cutinase enzymes, when incorporated in a sufficient amount into cleaning compositions, improve the cleaning ability of the composition. The present invention is directed to the further discovery that such microbial cutinase enzymes possess enzymatic activity at pHs in the range from about 6.5 to about 11; and that these enzymes are oxidatively stable in the presence of oxidants and are stable in the presence of other enzymes such as proteases. The present invention is still further directed to the discovery that such microbial cutinase enzymes synergistically interact with a plurality of surfactants in the cleaning compositions to improve the cleaning ability of the composition. The present invention is yet further directed to the discovery that cutinase is effective in hydrolyzing both cutin and cutin-like stains bound to a substrate such as a cloth garment.

Accordingly, in one of its composition aspects, the present invention is directed to an enzymatic cleaning composition for use in an aqueous solution comprising a microbial cutinase and a cleaning effective amount of a surfactant or a combination of surfactants compatible with said cutinase wherein said composition contains from about 0.01 percent to about 5.0 percent by weight of cutinase based on the weight of the surfactant and wherein the concentration of cutinase employed in said composition is sufficient so that upon dilution of said composition in said aqueous solution said solution comprises a cutinase concentration of at least 0.05 mg/liter.

In another of its composition aspects, the present invention is directed toward an enzymatic cleaning composition for use in an aqueous solution comprising a microbial cutinase derived from *Pseudomonas putida* (now reclassified as *Psuedomonas mendocina*) ATCC 53552, a protease and a cleaning effective amount of a surfactant or a combination of surfactants compatible with said cutinase, wherein said composition contains from about 0.01 percent by weight to about 5 percent by weight of cutinase based on the weight of the surfactant and wherein the specific concentration of cutinase employed in said composition is sufficient so that upon dilution of said composition in said aqueous solution said solution comprises a cutinase concentration from about 0.05 mg/liter to about 100 mg/liter and further wherein said protease is present in said composition in an amount from about 0.001 weight percent to about 5 weight percent based on the weight of the surfactant so that upon dilution in said aqueous solution said solution comprises a protease concentration from about 0.05 ppm to about 5 ppm.

In one of its method aspects, the present invention is directed to an improved method for enzymatically cleaning a material having a cutin or cutin-like stain which method comprises the steps of:

(a) selecting a cutinase enzyme;

(b) selecting a surfactant or a combination of surfactants compatible with said cutinase enzyme;

(c) forming an aqueous solution containing said enzyme and a cleaning effective amount of said surfactant or a combination of surfactants wherein said concentration of said enzyme in said solution is at least about 0.05 mg/liter;

(d) contacting the material with the solution of step (c); and (e) rinsing the material of step (d).

BRIEF DESCRIPTION OF THE DRAWINGS

FIG. 1 graphically correlates the activity of a preferred cutinase for use in this invention against pH.

FIG. 2 graphically correlates the activity of a preferred cutinase for use in this invention against temperature.

DETAILED DESCRIPTION OF THE INVENTION

The present invention is directed to the discovery that cutinase enzymes are useful when included in cleaning compositions. Cleaning compositions may take on a variety of forms such as for laundry cleaning, dishwashing, rug and upholstery cleaning, household and industrial cleaning, and the like. Common to each, however, is the presence of a cleaning effective amount of one or more surfactants. The surfactant(s) so employed is (are) compatible with the cutinase; that is to say that the surfactant(s) does (do) not significantly impair the activity of the cutinase. Accordingly, the cleaning compositions of this invention comprise a cleaning effective amount of a known surfactant or combinations of known surfactants and a microbial cutinase enzyme which can be added to an aqueous solution or to a solid powder, or formulated as an aqueous solution or solid powder and can be used to clean a wide variety of materials according to conventional cleaning techniques.

However, prior to discussing this invention in detail, the following terms will first be defined.

The term "surfactant" refers to a surface active agent, including non-ionic, anionic, cationic and zwitterionic surfactants well known for their use in cleaning compositions as well as to mixtures of one or more surfactants ("surfactant compositions").

Suitable anionic surfactants for use in the cleaning compositions of this invention include linear or branched alkylbenzenesulfonates; alkyl or alkenyl ether sulfates having linear or branched alkyl groups or alkenyl groups; alkyl or alkenyl sulfates; olefinsulfonates; alkanesulfonates and the like. Suitable counter ions for anionic surfactants include alkali metal ions such as sodium and potassium; alkaline earth metal ions such as calcium and magnesium; ammonium ion; and alkanol-amines having 1 to 3 alkanol groups of carbon no. 2 or 3.

Suitable cationic surfactants for use in the cleaning compositions of the present invention include quaternary ammonium salts including those having 3 to 4 alkyl substituents and up to 1 phenyl substituted alkyl substituents. Suitable counter ions for the cationic surfactants include halogen ions, hydroxide ions, and the like.

Nonionic surfactants generally comprise polyoxyalkylene ethers, as well as higher fatty acid alkanolamides or alkylene oxide adduct thereof, fatty acid glycerine monoesters, alkyl glucosides; and the like.

Zwitterionic surfactants include quaternary ammonium salt sulfonates, betaine-type ampholytic surfactants, and the like. Such zwitterionic surfactants have both the positive and negative charged groups in the same molecule.

Suitable surfactants for use in the present invention include those disclosed in U.S. Pat. Nos. 4,404,128 and 4,261,868, as well as in British Patent Application No. 2 094 826 A, the disclosures of which are incorporated herein by reference.

The amount of surfactant employed in the cleaning composition is dictated by the amount of cleaning composition to be added to the aqueous solution or solid powder. In general, if a large quantity of cleaning composition is to be added to the aqueous solution, then the concentration of surfactant in this composition required to achieve the desired concentration in the aqueous solution will be less than that required if a small quantity is to be employed. Accordingly, the amount of surfactant to be employed in the cleaning composition is necessarily related to the intended dilution range, i.e., to what extent will the cleaning composition be diluted when added to the aqueous solution. The balancing of the amount of surfactant to employ in the cleaning composition based on the intended dilution range is part of the ordinary skill in the art. In any event, the surfactant is generally employed from about 1 weight percent to about 95 weight percent based on the total weight of the cleaning composition and preferably, from about 5 weight percent to about 45 weight percent based on the total weight of the cleaning composition.

The term "cleaning effective amount of surfactant" means that the amount of surfactant employed in the cleaning composition is sufficient so that upon dilution of the cleaning composition into an aqueous solution, sufficient surfactant is present to effect cleaning of a fabric (material) added to this solution. In a preferred embodiment, the surfactant concentration in the aqueous solution should be at least about 0.2 mM and more preferably from about 0.2 mM to about 5 mM.

The term "cutinase compatible surfactant compositions" refer to surfactant compositions which, when added in a cleaning effective amount to an aqueous solution containing a cutinase, do not significantly impair the activity of the cutinase. In general, the determination of whether a surfactant composition is compatible with the cutinase can be readily ascertained by the following test. Specifically, the activity of 10 micromoles of cutinase in 1 liter of an aqueous solution at 30° C. and maintained at the pH optimum for the particular cutinase is measured using conventional techniques. Then, a cleaning effective amount of a surfactant composition is added to the aqueous solution and the activity of the cutinase is measured 15 minutes after addition of the surfactant composition. Surfactant compositions, which when added to the cutinase solution result in a 70 percent or greater reduction in cutinase activity as compared to the activity prior to addition of the surfactant composition, are said to be incompatible with the cutinase. On the other hand, if the addition of the surfactant composition reduces the activity of the cutinase by less than 70 percent as compared to the activity prior to addition of the surfactant or surfactant mixture, then the surfactant composition is compatible with the cutinase. Preferably, the surfactant composition will reduce the cutinase activity by no more than about 50 percent and, more preferably, by no more than about 30 percent.

As is apparent, reduction of the activity of the cutinase by the addition of the cutinase can be compensated for by increasing the concentration of the cutinase. That is to say that if the use of a specified amount of surfactant reduces the activity of cutinase by 50 percent, then doubling the amount of cutinase in the cleaning composition will offset this loss of activity.

The terms "microbial cutinase" and "cutinase" refer to cutinases derived from a microbial source, including bacterial and fungal sources. Such cutinases are well known in the art and are available from a wide variety of sources. See, for example, Kolattukudy, "Cutinases from Fungi and Pollen," in *Lipases*, Bergstrom et al Editors, Elsevier/North-Holland Publishing Co. Amsterdam, pp. 472–504, which is incorporated herein by reference for its discussion of cutinases useful in the practice of this invention. The particular cutinase employed in the compositions described herein is not important. A preferred cutinase, however, is one isolated from genetically engineered *Bacillus subtilis* expressing the *Pseudomonas mendocina* cutinase.

The natural substrate of cutinase is cutin which is a biopolyester polymer which covers the plant leaves, fruits, etc., see Kolattukudy, "Structure, Biosynthesis and Biodegradation of Cutin and Suberin," *Ann. Rev. Plant Physiol.*, Vol 32, pp. 539–567 (1981). Cutin is a high molecular weight (i.e., molecular weights of about 100,000 or more) biopolyester and cutinases are capable of hydrolyzing ester bonds in cutin thereby degrading the cutin polymer.

Cutinases are distinguishable from other lipases by methods well known in the art. See, for example, Purdy et al., "Cutinase Assay," *Biochemistry*, Vol. 14, pp. 2831–2840 (1975). Microbial cutinases from both fungal and bacterial sources have very good activity at pHs from about 6.5 to 12, preferably from about pH 8 to 11, which are an ideal pH condition for detergent use. In this regard, FIG. 1 illustrates that the cutinase activity of a preferred cutinase (isolated in a substantially pure form from *Pseudomonas mendocina*, ATCC 53552, described in U.S. Ser. No. 932,959 filed Nov. 19, 1986 and incorporated herein by reference) reaches a maximum at pH 7 but maintains about 80 percent or more of this maximum activity up to pH 11.

Cutinases, as opposed to lipases, are more specific for high molecular weight polyesters (e.g., cutin) than for low molecular weight esters such as triacyl glycerols (triglycerides) and possess less activity against triglycerides. See, for example, Sebastian et al., *J. of Bacteriology*, pp. 131–136 (January 1987). Contrarily, lipases are more specific for low molecular weight esters such as triglycerides and possess less activity against high molecular polyesters such as cutin.

The present invention is directed in part to the discovery that stains comprising lipids (e.g., triglycerides) and/or polymerized lipids bound onto a substrate such as cloth appear sufficiently similar to the natural substrate cutin that cutinase will hydrolyze such stains thereby removing the stains from the substrate. Without being limited to any theory, the binding of these stains to the substrate appears to be essential in allowing the cutinase to degrade the stain because, as noted above, cutinase is known in the art to be inactive and/or substantially less active against unbound triglycerides. See Sebastian et al., supra. Insofar as such bound stains are removed by cutinase, these stains are referred to as "cutin-like stains;" that is to say that cutin-like stains are those stains which when bound to a substrate sufficiently mimic cutin that cutinase is active against such stains.

Additionally, because cutinases employed herein generally possess greater stability at higher pHs, as well as greater oxidative stability as compared to lipases, cutinase is more effective than prior art lipases in removing these stains.

The substrate to which the lipid comprising stain is bound is any substrate which can chemically or physically bind the stain so as to produce a bound stain sufficiently similar to cutin that cutinase will hydrolyze it. Suitable substrates include, for example, cloth made of natural and/or synthetic fibers [such as cotton, wool, polyamide fibers (for example, nylon 6 and nylon 66), acrylic fibers (for example, polyacrylonitrile fibers), polyester fibers (for example, polyethylene terphthalate), polyvinyl alcohol fibers (for example, vinylon), polyolefin fibers (for example, polypropylene and polyethylene fibers), polyvinyl chloride fibers, polyvinylidene chloride fibers, polyurethane fibers, polyurea fibers and polyfluorocarbon fibers), glass, metals and the like. A particularly preferred substrate is cloth.

Preferably, the cutinase employed in the practice of this invention is substantially free of other enzymes and enzyme sources (e.g., less than about 30 weight percent and preferably less than about 10 weight percent of the cutinase is composed of non-cutinase protein sources) and includes the isolated enzyme broth containing the cutinase substantially free of other enzymes and enzyme sources.

Even more preferably, the cutinase employed in the practice of this invention is substantially pure (e.g., the isolated cutinase contains less than about 30 weight percent and preferably less than about 10 weight percent of non-cutinase enzyme and non-enzyme sources including non-enzyme sources such as the enzyme broth).

Cutinases, substantially free of other enzymes and enzyme sources, can be isolated and purified from the fermentation broth of the microbe using standard techniques. A particularly preferred cutinase for use in the present invention is that cutinase isolated in a substantially pure form from *Pseudomonas mendocina,* particularly, the *P. mendocina,* ATCC 53552, described in U.S. Ser. No. 932,959 filed Nov. 19, 1986 and incorporated herein by reference, which enzyme therefrom has the amino acid sequence of SEQ ID NO:1.

It should be understood that the microorganism of the present invention is not limited to the *P. mendocino* strain herein described, as natural and modified strains of the microorganism can be used. Mutant or variant strains of *P. mendocino* ATCC 53522 may be obtained by environmental selection pressure techniques, by UV irradiation, by the use of mutagenic chemicals or by genetic engineering.

In one embodiment, the cutinase having the above-noted amino acid sequence is isolated from a genetically engineered *E. coli* microorganism. See U.S. Ser. No. 07/705,052 by Gregory L. Gray, Ayrookaran J. Poulose and Scott D. Power entitled "Novel Hydrolase and Method" filed May 23, 1991 and incorporated herein in its entirety by reference.

In a preferred embodiment, the cutinase having the above-noted amino acid sequence is isolated from a genetically engineered *Bacillus subtilis* strain AK 1027.

Other sources of bacterial and fungal cutinases include, for example, *Fusarium solani pisi; Fusarium roseum sambucinum; Fusarium roseum culmorum; Helminthosporum sativum; Ulocladium consortiale; Streptomyces scabies; Colletotrichum capsici; Phytopthora cactorum; Botrytis cineria; Pestalotia subcuticularia; Venturia inequalis;* and *Colletotrichum gloeosporioides.*

The cutinase preparations of this invention can be prepared by cultivating the microorganisms described herein or other cutinase producing microorganisms under appropriate conditions. In order to obtain reasonable yields of enzyme, media containing readily assimilable carbon and energy sources, such as nitrogen source, are necessary as well as calcium and magnesium salts and trace elements and cutin, or monomers of cutin, or compounds resembling cutin or cutin monomers. One could also obtain the gene for cutinase and insert said gene into any organism of choice so that the organism expresses cutinase. Under these circumstances, it would not be necessary to add cutin or cutin monomers into the fermentation.

The addition of cutinase to conventional cleaning compositions does not create any special use limitation. In other words, any temperature and pH suitable for detergent compositions containing enzymes is also suitable for the present invention.

The cutinase employed in the cleaning compositions of this invention should preferably be selected to cause at least about 10 percent, and more preferably at least 20 percent, hydrolysis of the given fat under given conditions. Normally, the amount of cutinase in the cleaning composition is in a concentration from about 0.01 weight percent to about 5.0 weight percent of the surfactant, and preferably, from about 0.05 weight percent to about 3 weight percent. The specific concentration of cutinase employed in the cleaning composition is selected so as to provide a cutinase concentration upon dilution in the aqueous solution of at least about 0.05 mg/liter and preferably, from about 0.05 mg/liter to about 100 mg/liter. At lower cutinase concentrations, the cleaning benefits against cutin and cutin-like stains are particularly evident with repeated washings of the stained material.

When employed in such concentrations, the cutinases exhibit cleaning activity in the aqueous wash solution, especially when employed from 20° to 50° C. In this regard, FIG. 2 illustrates that significant enzymatic activity is achieved for a preferred cutinase (isolated in a substantially pure form from *Pseudomonas mendocina,* ATCC 53552, described in U.S. Ser. No. 932,959 filed Nov. 19, 1986 and incorporated herein by reference) over a temperature range from about 12° C. to about 55° C.

One skilled in the art could take the preferred cutinase or, for that matter, any cutinase of the invention or any immunologically identical cutinase and use random or selective replacement of amino acids to produce other cutinases which are more or less selective toward given substrates or include modification in activity such as oxidative stability, increased enzymatic activity, activity against different stains, and the like.

CLEANING COMPOSITIONS AND METHODS OF USE

Cleaning compositions containing cutinase will work especially well on gravy, oils and greases bound to a substrate, plant or grass bound to a substrate, oil based makeup bound to a substrate and collar stains.

Cutinases can be formulated as a purposefully added ingredient into known powdered and liquid cleaning compositions having a pH between 6.5 and 12.0 at levels of about 0.01 to about 5 weight percent and preferably, between about 0.05 and 0.5 weight percent based on the weight of surfactant. It has been discovered that cutinases are ideal for inclusion into cleaning compositions. Specifically, cutinases are oxidatively stable to oxidants such as $H_2O_2$. They have good stability for up to at least one hour in a temperature range of from about 20° C. to 50° C. which is ideal for cleaning solutions. See, for example, FIG. 2. They are also stable in the presence of other enzymes; e.g., proteases, and as such, are ideal for mixtures of enzymes. See, for example, Example 1 set forth hereinbelow.

Because of the specific activity of cutinases, it is a preferred aspect of the present invention to combine into the cleaning compositions one or more cutinases with one or more other enzymes such as proteases, amylases or other lipases.

Further, it has been discovered that a synergistic increase in hydrolytic activity of cutinase occurs when the cutinase is combined with two or more surfactants.

In general, the requisite amount of the cleaning composition is added to an aqueous solution so as to achieve the concentration of surfactant and cutinase discussed above. In this regard, the cleaning composition is purposely formulated by selecting an appropriate cutinase and a surfactant or a combination of surfactants compatible with the cutinase. The material to be cleaned is also added to the aqueous cleaning solution either prior to or subsequent to the addition of the cleaning composition. After suitable treatment time, often accompanied by agitation, the material is then rinsed so as to provide a cleaned material.

Preferably, the cleaning composition for use in the methods described herein is a detergent cleaning composition suitable for laundry use and dishwashing. In addition to the surface active agent and the cutinase, the detergent compositions of this invention can additionally contain the following components:

HYDROLASE EXCEPT CUTINASE

Such hydrolases include proteases, amylases, cellulases and other lipases. The hydrolase is incorporated into the detergent composition, as much as required, according to the intended purpose. Suitable hydrolases are well known in the art. When employed the particular enzyme is preferably incorporated in an amount of 0.001 to 5 weight percent, and more preferably 0.02 to 3 weight percent, in terms of pure enzyme and based on the weight of the surfactant. The specific amount of enzyme employed is selected so as to achieve its intended purpose. For example, with a protease, the amount employed is generally selected so as to provide a protease concentration in the aqueous medium from about 0.05 ppm to about 5 ppm and preferably from about 0.1 ppm to about 2 ppm.

Such enzymes can be used in the form of granules made of crude enzyme alone or in combination with other components in the detergent composition. Granules of crude enzyme are used in such an amount that the purified enzyme is 0.001 to 50 weight percent in the granules. The granules are used in an amount of 0,002 to 20 and preferably 0.1 to 10 weight percent. In order to prevent inactivation of the enzyme(s) by other components in the cleaning composition, it is common to coat the enzyme (including the cutinase) with an inert material soluble in water. When added to water, the inert material is dissolved so as to free the enzyme. See for instance, U.S. patent application Ser. No. 07/642,669, filed Jan. 17, 1991 and entitled "Granules Containing Both an Enzyme and an Enzyme Protecting Agent and Detergent Compositions Containing Such Granules," which application is incorporated herein by reference in its entirety. Likewise the granules can be formulated so as to contain materials to reduce the rate of dissolution of the granules into the wash medium such materials and granules are discussed in U.S. patent application Ser. No. 07/642,596 filed on Jan. 17, 1991 and entitled "Granular Compositions," which application is incorporated herein by reference in its entirety.

PEROXIDASE

The peroxidase could include, for example, microbial peroxidase such as ligninase and plant peroxidases such as, for example, horseradish peroxidase. The cleaning composition may contain from about 50 to about 10,000 ppm of one or more of the peroxidases for a final concentration of 0.1 to about 10 ppm of one or more of the peroxidases in the aqueous solution.

LONG-CHAIN FATTY ACID SALTS

Long-chain fatty acid salts include saturated or unsaturated fatty acid salts, alkyl or alkenyl ether carboxylic acid salts, -sulfofatty acid salts or esters, amino acid-type surfactants, phosphate ester surfactants and the like. Suitable long-chain fatty acid salts are disclosed in British Patent Application No. 2 094 826 A, the disclosure of which is incorporated herein by reference. The composition may contain from about 1 to about 20 weight percent of such long-chain fatty acid salts.

BUILDERS

A. Divalent sequestering agents:

The composition may contain from about 0 to about 50 weight percent of one or more builder components selected from the group consisting of alkali metal salts and alkanolamine salts of the following compounds: phosphates, phosphonates, phosphonocarboxylates, salts of amino acids, aminopolyacetates, high molecular electrolytes, non-dissociating polymers, salts of dicarboxylic acids and aluminosilicate salts. Suitable divalent sequestering agents are disclosed in British Patent Application No. 2 094 826 A, the disclosure of which is incorporated herein by reference.

B. Alkalis or inorganic electrolytes:

The composition may contain from about 1 to about 50 weight percent, preferably from about 5 to about 30 weight percent, based on the composition of one or more alkali metal salts of the following compounds as the alkalis or inorganic electrolytes: silicates, carbonates and sulfates as well as organic alkalis such as triethanolamine, diethanolamine, monoethanolamine and triisopropanolamine.

ANTIREDEPOSITION AGENTS

The composition may contain from about 0.1 to about 5 weight percent of one or more of the following compounds as antiredeposition agents: polyethylene glycol, polyvinyl alcohol, polyvinylpyrrolidone and carboxymethylcellulose.

BLEACHING AGENTS

The use of the cutinase of the present invention in combination with a bleaching agent, i.e., an oxidizing agent, such as sodium percarbonate, sodium perborate, sodium sulfate/hydrogen peroxide adduct and sodium chloride/hydrogen peroxide adduct or/and a photo-sensitive bleaching dye such as zinc or aluminum salt of sulfonated phthalocyanine further improves the derging effects. Without being limited to any theory, it is believed that such improvement is the result of the oxidative stability of the cutinase in the presence of such oxidizing agents.

BLUING AGENTS AND FLUORESCENT DYES

Various bluing agents and fluorescent dyes may be incorporated in the composition, if necessary. Suitable bluing agents and fluorescent dyes are disclosed in British Patent Application No. 2 094 826 A, the disclosure of which is incorporated herein by reference.

CAKING INHIBITORS

The following caking inhibitors may be incorporated in the powdery detergent: p-toluenesulfonic acid salts, xylenesulfonic acid salts, acetic acid salts, sulfosuccinic acid salts, talc, finely pulverized silica, clay, calcium silicate (such as Micro-Cell of Johns Manville Co.), calcium carbonate and magnesium oxide.

ANTIOXIDANTS

The antioxidants include, for example, tert-butyl-hydroxytoluene, 4,4'-butylidenebis (6-tert-butyl- 3-methylphenol), 2,2'-butylidenebis (6-tert-butyl- 4-methylphenol), monostyrenated cresol, distyrenated cresol, monostyrenated phenol, distyrenated phenol and 1,1-bis (4-hydroxyphenyl) cyclohexane.

SOLUBILIZERS

Solubilizers may be incorporated into the compositions of this invention. Suitable solubilizers include, for example, lower alcohols such as ethanol, benzenesulfonate salts, lower alkylbenzenesulfonate salts such as p-toluenesulfonate salts, glycols such as propylene glycol, acetylbenzenesulfonate salts, acetamides, pyridinedicarboxylic acid amides, benzoate salts and urea.

Aside from the above ingredients, perfumes, buffers, preservatives, dyes and the like can be used, if desired, with the detergent compositions of this invention.

When a cleaning composition used in the present invention is in the form of a powder, it may be one which is prepared by any known preparation method including a spray-drying method and a granulation method. The cutinase of the invention may be added to the cleaning composition in the form of granulates or prills, prepared in the methods known in the art such as described in British Patent Nos. 1,324,116 and 1,362,365, as well as U.S. Pat. Nos. 3,519,570, 4,106,991 and 4,242,219, the disclosures of which are incorporated herein by reference. In some cases, it may be desirable to coat the cutinase with an inert material in order to prevent one or more ingredients in the powdery detergent formulation from inactivating the cutinase.

When the cleaning composition is a liquid, it may be either a homogeneous solution or an inhomogeneous dispersion. The cutinase of the present invention is added directly to the liquid and preferably, in order to prevent one or more ingredients from inactivating the cutinase, the cutinase is coated with an inert material.

The following examples are offered to illustrate the present invention and should not be construed in any way as limiting the scope of this invention.

EXAMPLES

EXAMPLE 1

Stability of Cutinases against Proteases

The present example tests the stability of cutinase in an aqueous solution with or without the presence of a protease.

A. In part A of this example, the cutinase employed was that cutinase isolated in a substantially pure form from *P. mendocina,* ATCC 53552, described in U.S. Ser. No. 932,959 filed Nov. 19, 1986 and incorporated herein by reference and the protease employed was either Maxacal™ (a substilisin protease available from Gist-Brocade, N.V., Delft, Holland) or Esperase™ (a protease available from Novo Industries, Copenhagen, Denmark).

In this example aqueous test solutions containing 42 µg/ml of cutinase and either 35 µg/ml (Maxacal™) or 64 µg/ml (Esperase™) of protease were prepared. The solutions were buffered to pH 10 with 0.1M sodium phosphate. The solutions were incubated at 37° C. and the enzymatic activity of cutinase was periodically monitored by the hydrolysis of a model cutinase substrate p-nitrophenyl butyrate as measured by the absorbance change at 410 nm in 100 mM Tris buffer containing 0.1% Triton X-100 at pH 8. This value correlated against a standard, i.e., an aqueous solution containing cutinase but no protease. Diminishment in the enzymatic activity of the cutinase in the test solutions as compared to the standard is attributed to degradation of the cutinase by the protease. The results of this tests are set forth in Table 1 as follows:

TABLE 1

| Protease | CUTINASE ACTIVITY AFTER TIME[1] | | | | |
|---|---|---|---|---|---|
| | 0 min | 5 min | 10 min | 15 min | 840 min |
| Standard[2] | 1.57 | 1.60 | 1.47 | 1.63 | 1.61 |
| Maxacal ™ | 1.68 | 1.58 | 1.72 | 1.66 | 0.134 |

TABLE 1-continued

| Protease | CUTINASE ACTIVITY AFTER TIME[1] | | | | |
|---|---|---|---|---|---|
| | 0 min | 5 min | 10 min | 15 min | 840 min |
| Esperase ™ | 1.73 | 1.64 | 1.59 | 1.51 | 0.456 |

[1]Activity reported in absorbance change at 410 nm when a model cutinase substrate, p– nitrophenyl butyrate, is hydrolyzed. Higher values correspond to more enzymatic activity.
[2]Standard did not contain any protease.

B. In part B of this example, the cutinase employed was the same as in part A above whereas the protease employed was either Alcalase™ (an alkaline protease available from Novo Industries, Copenhagen, Denmark), a mixture of Alcalase™ and Savinase™ (an alkaline protease available from Novo Industries, Copenhagen, Denmark), or a mixture of Savinase™ and Esperase™ (a protease available from Novo Industries, Copenhagen, Denmark).

In this example, aqueous test solutions containing cutinase contained 2 µg/ml of cutinase and the amount of protease specified in Table 2 below. The solutions were incubated at 37° C. for 28 minutes at pH 10 and the enzymatic activity of cutinase was periodically measured in a pH stat by the hydrolysis of trioctanoin in a 0.5 percent trioctanoin and a 0.05 percent sodium dodecyl sulfate emulsion. The measured value was correlated against a standard, i.e., an aqueous solution containing cutinase but no protease. Diminishment in the enzymatic activity of the cutinase in the test solutions as compared to the standard is attributed to degradation of the cutinase by the protease. The results of this tests are set forth in Table 2 as follows:

TABLE 2

| | | CUTINASE ACTIVITY IN THE AQUEOUS SOLUTION AFTER 28 MINUTES | |
|---|---|---|---|
| Cutinase | Protease | Conc. of Protease (µg/ml) | Activity[3] |
| — | — | — | 4.5 |
| — | Alcalase/Savinase | 17.7/20.0 | 6.4 |
| — | Esperase/Savinase | 15.3/15.7 | 5.9 |
| Yes | — | — | 417.8 |
| Yes | Alcalase | 34.7 | 420.3 |
| Yes | Alcalase/Savinase | 17.7/20.0 | 428.0 |
| Yes | Esperase/Savinase | 15.0/13.0 | 411.0 |

[3]Activity reported in units of octanoic acid released by the hydrolysis of trioctanoin. Higher values correspond to more enzymatic activity.

The results from A and B above demonstrate that cutinase is stable in an aqueous solution in the presence of a protease over periods of time commonly encountered in cleaning use, especially in laundry use.

EXAMPLE 2 pH stability of Bacterial Cutinase

In this example the half-life of the same cutinase used in Example 1 above was measured at 50° C. at various pHs. Specifically, cutinase was introduced into a 0.1M sodium phosphate buffer at the pH specified below and the activity was measured by hydrolysis of trioctanoin in polyvinyl alcohol emulsions. The time required for the activity to diminish to ½ of its initial value is taken as the half-life at that particular pH. The results of these tests are set forth in Table 3 as follows:

TABLE 3

| HALF-LIFE AT 50° C. (in minutes) | |
|---|---|
| pH | Half-Life |
| 7 | 1800 |
| 8 | 1500 |
| 9 | 720 |
| 10 | 18 |

The above data demonstrates that the cutinase activity is sufficiently stable in neutral and alkaline pHs so as to be useful in cleaning compositions. The above data further demonstrates that at higher pHs, i.e., pH 10 and greater, it may be desirable to employ a higher concentration of cutinase in order to compensate for some loss of enzymatic activity at these conditions.

EXAMPLE 3

Effect of Surfactants on Hydrolase Activity

This example measures the effect of surfactants (detergents) on the hydrolytic activity of cutinase. Specifically, in this example, an aqueous solution was prepared so as to contain 120 nanomoles per liter of cutinase (isolated in a substantially pure form from *P. mendocina*, ATCC 53552, described in U.S. Ser. No. 932,959 filed Nov. 19, 1986 and incorporated herein by reference); and 0.1 moles/liter of Tris [Tris(hydroxymethyl)aminomethane] buffer maintained at pH 8.0 and 25° C. In some cases, surfactant [sodium dodecyl sulfate (SDS) and/or Triton X-100™ (octoxynol), available from Rohn & Haas, Philadelphia, Pa.] was then added in the amount specified in Table 4 below. In this example, the enzymatic activity of the cutinase was measured in these solutions using the amount of p-nitrophenol generated from the p-nitrophenylbutyrate substrate as measured by following the absorbance of p-nitrophenol at 410 nm. The enzymatic activity of the cutinase under the above conditions and in the absence of surfactant is arbitrarily assigned a value of 100 percent and enzymatic activity of the other test solutions are reported as a percentage of the standard. The results are reported in Table 4 below:

TABLE 4

| Surfactant[4] Triton X-100 | SDS | Percent Activity |
|---|---|---|
| 0 | 0 | 100 |
| 0.2 | 0 | 78 |
| 0.4 | 0 | 60 |
| 0 | 0.05 | 30 |
| 0 | 0.1 | 23 |
| 0 | 0.2 | 14 |
| 0 | 0.4 | 6 |
| 0.4 | 0.4 | 78 |
| 0.2 | 0.2 | 98 |
| 0.2 | 0.05 | 125 |
| 0.2 | 0.1 | 138 |
| 0.1 | 0.1 | 130 |
| 0.05 | 0.05 | 132 |

[4]The concentration of surfactant in the aqueous solution is reported in weight percent based on the weight of the aqueous solution.

The above results demonstrate that, at the concentrations tested, the non-ionic surfactant (Triton X-100) is compatible with the cutinase whereas the ionic surfactant (sodium dodecyl sulfate) is not. The above results further demonstrate that combinations of anionic and non-ionic surfactants are compatible with the enzyme and that a synergistic result is achieved wherein the cutinase activity in the surfactant combination is greater than the sum of the cutinase activity in the presence of either surfactant alone.

EXAMPLE 4

Removal of Cutin-Like Stains from a Substrate by Cutinase

A. The following example is taken from European Patent Application No. 0 399 681 by Maha Y. El-Sayed et al. (published on Nov. 28, 1990) and incorporated herein by reference. The example demonstrates that cutinase can remove cutin-like stains from a substrate. Specifically, and as noted above, cutin-like stains comprise lipids (e.g., triglycerides) bound onto a substrate such as cloth and which appear sufficiently similar to the natural substrate cutin that cutinase will hydrolyze such stains thereby removing the stains from the substrate.

In this example, a cleaning composition is prepared by admixing a non-ionic surfactant (Neodol 23-6.5—available from Shell) and a non-ionic surfactant (Surfonic JL-80X—available from Texaco) in a 1:0.2 mole ratio. In particular, the cleaning composition contains the following components:

| Component | Wt. Percent |
|---|---|
| Surfactant Neodol 23-6.5 | 3.7 |
| Surfonic JL-80X | 26.0 |
| Deionized Water | 0.6 |
| Sodium Tripolyphosphate | * |
| Sodium Carbonate | 10.5 |
| Sodium Polysilicate[5] | 1.5 |
| Alkaline Proteases[6,7] | 0.8/0.6 |
| Brightner[8] | 0.9 |
| Pigment | 0.1 |
| Fragrance | 0.2 |

*The amount is not provided in EPO Application No. 0 399 681 A2 but is believed to be the remainder necessary to bring the weight percent of the composition to 100.
[5]Trademark Britesil, available from PQ Corp.
[6]Trademark Alcalase, available from Novo Ind.
[7]Trademark Savinase, available from Novo Ind.
[8]Trademark Tinopal 5BM-XC, available from Ciba Geigy A.G.

To an identical cleaning composition, as described above, is added sufficient cutinase (isolated in a substantially pure form from *P. mendocino*, ATCC 53552, described in U.S. Ser. No. 932,959 filed Nov. 19, 1986 and incorporated herein by reference) so that upon dilution in the aqueous wash solution, the solution contains 2 ppm cutinase (A) or 20 ppm (B).

A. The substrates employed in this example are cotton swatches stained with a synthetic sebum soil which forms a cutin-like stain. The synthetic sebum soil was prepared from a mixture of oils containing:

| Oils | % W/W |
|---|---|
| Stearic acid | 5% |
| Squalene | 5% |
| Cholesterol | 5% |
| Linoleic acid | 5% |
| Oleic acid | 10% |
| Paraffin acid | 10% |
| Palmitic acid | 10% |
| Coconut oil | 15% |

-continued

| Oils | % W/W |
|---|---|
| Sperm wax | 15% |
| Olive oil | 20% |

To 15 grams of the above-melted oils was added 0.6 grams of oleic acid, 1.2 grams triethanolamine and 0.225 grams of charcoal. Then, 60 ml of water is admixed, and the mixture blended for one minute and the resulting mixture was used to stain the swatches.

The cotton swatches stained as above were then washed in test beakers by agitating for 14 minutes followed by a five minute rinse. The cleaning composition employed was 0.205 grams of the cleaning composition described above (containing the cutinase) dissolved in 250 ml of water. A control was also prepared by dissolving 0.205 grams of the cleaning composition (without cutinase) in 250 ml of water and cotton swatches were treated with this solution using the same protocol as above. The results of this test are set forth as follows:

| Cleaning Composition | Percent Stain Removed |
|---|---|
| Control | 57.37 |
| Control + Cutinase | 60.72[9] |

[9]LSD = 2.23 at 0.95 confidence level.

B. Polyester swatches were stained with sebum, vegetable oil or olive oil. These swatches were then washed for 12 minutes at 96° F. in a 72 liter washing machine, rinsed in the normal rinse cycle and then are allowed to air dry. One set of swatches was treated in an aqueous solution having 59 grams of the cleaning composition described above (with cutinase) while another set of swatches was treated with the cleaning composition described above (without cutinase ), e.g., control. The results of this test are shown in Table 5 below:

TABLE 5

| | PERCENT STAIN REMOVED | | |
|---|---|---|---|
| | Stain | | |
| Cleaning Composition | Sebum[10] | Vegetable[11] Oil | Olive[12] Oil |
| Control | 83.75 | 29.20 | 35.05 |
| Control + Cutinase | 89.69 | 51.82 | 60.79 |

[10]LSD = 1.52 at 0.95 confidence level.
[11]LSD = 6.08 at 0.95 confidence level (Wesson brand oil).
[12]LSD = 5.60 at 0.95 confidence level.

The above data demonstrates that more of the lipid comprising stain (e.g., fatty acids, oils, etc.) is removed from the substrate when a cutinase is employed in the cleaning composition than when a cutinase is not employed. Without being limited to any single theory, it is believed that when the lipid binds to the substrate, the lipid/substrate structure mimics the structure of cutin so as to produce a cutin-like stain that the cutinase will act upon.

EXAMPLE 5

Stability of Cutinase to Oxidants

This example demonstrates the stability of cutinase in aqueous solutions to oxidation in the presence of oxidants, such as oxidants commonly encountered in cleaning compositions. Specifically, in this example, an aqueous solution of 0.5 mg/ml of cutinase (isolated in a substantially pure form from *P. mendocina*, ATCC 53552, described in U.S. Ser. No. 932,959 filed Nov. 19, 1986 and incorporated herein by reference) containing 0.1M sodium phosphate buffer was incubated in varying amounts of hydrogen peroxide wherein the aqueous solution was maintained at pH 8.4 and at 25° C. for two hours. The enzymatic activity of the cutinase under the above conditions and in the absence of hydrogen peroxide is arbitrarily assigned a value of 100% and enzymatic activity of the other test solutions are reported as a percentage of the standard. The results are reported in Table 6 below:

TABLE 6

| Concentration of Hydrogen Peroxide (in ppm) | Percent Cutinase Activity |
|---|---|
| 0 | 100% |
| 100 | 86% |
| 200 | 86% |
| 500 | 91% |
| 1000 | 95% |

The above data demonstrates that cutinase activity is sufficiently stable in the presence of an oxidant so as to be useful in cleaning compositions.

EXAMPLE 6

Removal of Cutin-like Stains from an Insoluble Support Matrix

The substrate was prepared by diluting 1 mCi of $^3$H-Triolein (0.5 mCi/ml, 26.8 Ci/nmol) into 17 ml isopropanol containing 421 mg of non-$^3$H-Triolein. The final concentration was about 23–24 mg Triolein/ml. This was divided into 1 ml aliquots and stored.

Polyester cloth swatches cut into approximately ½ inch×½ inch squares were laid onto a glass plate. 3 µl of the above mixture was pipetted onto each swatch and allowed to air dry.

A solution comprising 1 percent fatty acid free bovine serum albumin (BSA), and 100 mM of a suitable buffer, preferably Tris (pH range 6 to 9) or glycine (pH range 8 to 11) was allowed to equilibrate to a fixed temperature (preferably 32° C.) in a shaking water bath. An aliquot of cutinase (0.25 to 1.5 µg/ml) was then added to 2.8 ml of the BSA solution, followed by the insertion of four of the cloth swatches, taking care to keep the swatches as separate as possible. The cutinase added was isolated from *Fusarium solani pisi, Colletotrichum capsici, Pseudomonas mendocina* or *Pestalotia subcuticularia*. The entire mixture was then allowed to shake in the constant temperature bath at 150 rpm for 15 minutes.

An aliquot of the liquor, preferably 20% of the entire volume was pipetted into a scintillation vial containing 10 ml of Ecolume™ scintillation fluid. After chilling, the scintillation vials were counted. The counts found free in the solution are a direct measure of the fatty acid hydrolyzed from the solid surface by the lipase.

TABLE 7

| SOURCE | TRIOLEIN HYDROLYSIS (cnts./10 min.) | SP. ACTIVITY TRIOLEIN HYDROLYSIS (cnts./10 min./μg enzyme |
|---|---|---|
| F. solani pisi 1 | 1,847 | 41,977 |
| F. solani pisi 2 | 927 | 29,711 |
| C. capsici | 16,923 | 165,250 |
| P. subcuticularia | 1,168 | 13,150 |
| P. mendocino | 9,250 | 157,045 |

EXAMPLE 7

Expression of Cutinase in *Bacillus subtilis* and a Comparison to Expression in the Native Organism The gene for the *Pseudomonas mendocina* cutinase described in U.S. Ser. No. 932,959 filed Nov. 19, 1986 was transferred into *Bacillus subtills* as a fusion with the *Bacillus subtills* aprE gene. The resultant strain was compared under optimal shake flask conditions with the original *Pseudomonas mendocina* isolate using the following assay:

Assay: *Pseudomonas mendocina* cutinase is assayed with 1 mM p-nitrophenylbutyrate in 0.2M Hepes buffer at pH 7.0. The activity is expressed as change in absorbance at 410 nm/min/10 μl sample in a 1 mL reaction volume. Construction of *Bacillus subtills* strain AK1027:

The following synthetic primers were used for the mutagenesis:

| 1 | 5'CCACTGTCGCTGCAGGAAAAGCTCCCCTGC 3' | SEQ ID NO: 2 |
| 2 | 5'GCAGGCTGCAGGAAAAAGCA 3' | SEQ ID NO: 3 |
| 3 | 5'TGCGCAGGCTGCTCCCCTGC 3' | SEQ ID NO: 4 |

The cutinase gene (U.S. patent application Ser. No. 07/629,308 filed Dec. 18, 1990) was cloned into a M13 plasmid as an XbaI-SphI fragment and a PstI site was introduced at the beginning of the mature coding sequence by site-directed mutagenesis (T. A. Kunkel, *PNAS* [1985], Vol. 82, pp. 488–492) using single-stranded synthetic primer 1 (SEQ ID NO:2). The aprE gene from pS168-1 (M. L. Stahl et al., *J. Bact.* [1984], vol. 158, pp. 411– 418) was cloned into another M13 plasmid as an EcoRI-HindIII fragment and a PstI site was introduced after the signal sequence with single-stranded synthetic primer 2 (SEQ ID NO:3) using the same technique. The method of cloning the DNA fragments is provided in Sambrook et al. *Molecular Cloning a Laboratory Manual* (1989) pp. 1.53–1.73 and pp. 4.3–4.51. The EcoRI-PstI fragment of aprE and the PstI-SphI fragment of the cutinase gene were isolated from the M13 plasmids and cloned into an EcoRI-SphI digested JM102 vector (E. Ferrari et al., *J. Bact.* (1983) Vol. 154, pp. 1513–1515) creating pAprcut-1.

To introduce a strong transcriptional terminator the aprE-cutinase fusion gene fragment from pAprcut-1 was cloned as follows into pJH101 (E. Ferrari et al., *J. Bact*, Vol. 154, pp. 1513–1515) which had been constructed to contain the *Bacillus amyloliquefaciens* subtilisin transcriptional terminator on a HindIII-BamHI fragment (Wells et al., *Nucleic Acid Research* (1983), Vol. 11, pp. 7911–7925). The EcoRI-PvuII DNA fragment containing the aprE promotor and signal sequence and the 5' end of the cutinase gene and the PvuII-AvaI DNA fragment containing the 3' end of the cutinase gene were isolated from pAprcut-1. The AvaI 5' overhang of the PvuII-AvaI fragment of the cutinase gene was filled in by T4 polymerase (Sambrook et al. *Molecular Cloning a Laboratory Manual*). The plasmid pJH101 with the terminator was digested with EcoRI-HindIII and the HindIII 5' overhang was also filled in with T4 polymerase. The EcoRI-PvuII fragment, the PvuII-AvaI fragment and the EcoRI-HindIII digested pJH101 were ligated to create pAprcut-2.

Next, the mature cutinase gene was fused directly to the aprE signal sequence by site-directed mutagenesis. The EcoRI-Asp718 fragment of pAprcut-2 containing the signal sequence was cloned into a M13 plasmid and the cutinase gene was fused directly to the signal sequence by site-directed mutagenesis using single-stranded synthetic primer 3 (SEQ ID NO:4). After mutagenesis the EcoRI-Asp718 fragment containing the signal sequence directly fused to the 5' end of the cutinase gene was isolated from the M13 plasmid. This fragment was used to replace the original EcoRI-Asp718 fragment of pAprcut-2 which contained the aprE signal not directly fused to the cutinase gene. The new plasmid with the directly fused gene was called pAprcut-3.

The pAprcut-3 plasmid was used to transform *Bacillus subtills* strain BB8 (C. Anagnostopoulos, *J. Bact.* [1961], Vol. 81, pp. 741–746) and the plasmid was integrated into the chromosome specifically in the aprE locus by the Campbell-type mechanism (M. Young, *J. Gen. Microbiol.* [1984], Vol. 130, pp. 1613–1621). The Bacillus strain BB8 used had four protease genes deleted, the estB gene deleted and the isp gene inactivated (delta apr, delta npr, delta bpF, delta epr, isp-1, delta estB). Deletion of the genes indicated was done using the method described by M. L. Stahl et al. in *J. Bact.* [1984], Vol. 158, pp. 411–418. The sacU32(Hy) mutation (D. J. Henner et al., *J. Bact.* [1988], Vol. 170, pp. 296–300) was introduced by PBS-1 mediated transduction (J. A. Hoch et al., *J. Bact.* [1967], Vol. 93, pp. 1925–1937), after transformation with pAprcut-3 creating the AK1027 strain.

Cultivation and yield of cutinase from *Pseudomonas mendocina*:

*Pseudomonas mendocina* was grown overnight at 35° C. with shaking in medium A. The overnight culture was diluted 1/20 into the production medium (B) and allowed to grow until maximum production was observed (48 hrs.).

Cultivation and yield of cutinase from *Bacillus subtilis* strain AK1027:

The Bacillus strain was grown overnight in Medium C at 37° C. with shaking. Part of the overnight culture was diluted 1/20 into Medium D and the production of cutinase followed until the maximum point was reached (24 hrs.)

TABLE 8

| Medium A | |
|---|---|
| Nutrient Broth (Difco) | 0.6% |
| Glucose | 1.0% |
| Medium B | |
| Apple cutin | 0.3% |
| Nutrient Broth (Difco) | 0.6% |
| Yeast extract (Difco) | 0.2% |

TABLE 8-continued

| | |
|---|---|
| pH adjusted to 8.5 | |
| Medium C | |
| Penassay broth (Difco) | |
| Medium D | |
| Soy Peptone (Marcor) | 5% |
| Maltodextrin (Staley 200) | 10% |
| $CaC_{12}$ | 1 mM |
| Dextrose | 0.07% |
| $MgSO_4$ | 2 mM |
| $Na_2HPO_4$ | 1 mM |
| $K_2HPO_4$ | 40 mM |
| $KH_2PO_4$ | 20 mM |

TABLE 9

| | Results |
|---|---|
| Strain | Yield |
| *Pseudomonas mendocina* | 0.0363 units/10 µl |

TABLE 9-continued

| | Results |
|---|---|
| Strain | Yield |
| *Bacillus subtilis* AK1027 | 0.4480 units/10 µl |

Summary: *Bacillus subtills* AK1027 with pAKaprlip on the chromosome produces 0.448 units/10 µl versus 0.036 units/10 µl for the original Pseudomonas strain. This represents an improvement of over fold relative to the original strain and offers the advantage of a shorter production time by 50 percent.

Although the preferred form of the invention has been described above, it will be obvious to those skilled in the art to which this invention pertains, that, various changes and equivalent modifications may be made without parting from the scope of the invention as defined by the claims.

What is claimed is:

1. An enzymatic cleaning composition for use in an aqueous solution consisting of a microbial cutinase and a cleaning effective amount of a non-ionic surfactant or a combination of non-ionic surfactants compatible with said cutinase wherein said composition comprises from about 0.01 percent to about 5.0 percent by weight of cutinase based on the weight of the non-ionic surfactant wherein the weight of the cutinase employed in said composition is sufficient so that upon dilution in said aqueous solution there is sufficient cutinase so as to achieve a cutinase concentration of at least 0.05 mg/liter.

2. A composition according to claim 1 wherein said cutinase is present in an amount from about 0.05 percent by weight to about 3 percent by weight based on the weight of surfactant.

3. A composition according to claim 2 wherein the cutinase is derived from *Pseudomonas mendocina*, ATCC 53552.

4. A composition according to claim 3 wherein the cutinase is substantially free of other enzymes and enzyme sources.

5. A composition according to claim 4 wherein the cutinase is isolated as a substantially pure microbially produced cutinase.

6. An enzymatic composition for use in an aqueous solution consisting of a microbial cutinase and one or more enzymes selected from the group consisting of lipases, amylases, cellulases, peroxidases and proteases, and a cleaning effective amount of a non-ionic surfactant or a combination of non-ionic surfactants compatible with said cutinase wherein said composition comprises from about 0.01 percent to about 5.0 percent by weight of cutinase based on the weight of the non-ionic surfactant where the weight of the cutinase employed in said composition is sufficient so that upon dilution in said aqueous solution there is sufficient cutinase so as to achieve a cutinase concentration of at least 0.05 mg/liter.

7. A composition according to claim 1 wherein said cutinase is capable of causing hydrolysis of at least 10 percent by weight of a stain comprising a lipid or polymerized lipid.

8. A composition according to claim 1 wherein said cutinase is a non-naturally occurring cutinase having at least one amino acid randomly or selectively replaced by an amino acid not naturally found at that position.

9. An enzymatic cleaning composition for use in an aqueous solution comprising a microbial cutinase derived from *Pseudomonas mendocina*, ATCC 53552, a protease and a cleaning effective amount of a non-ionic surfactant or a combination of non-ionic surfactants compatible with said cutinase, wherein said cutinase is present in said composition in an amount from about 0.01 weight percent to about 5 weight percent based on the weight of the surfactant wherein the weight of cutinase employed in said composition is sufficient so that upon dilution in said aqueous solution there is sufficient cutinase so as to achieve a cutinase concentration from about 0.05 mg/liter to about 100 mg/liter and further wherein said protease is present in said composition in an amount from about 0.001 weight percent to about 5 weight percent based on the weight of the surfactant and present in an amount such that upon dilution in said aqueous solution there is sufficient protease so as to achieve a protease concentration from about 0.05 ppm to about 5 ppm.

10. An improved method for enzymatically cleaning a material having a stain comprising a lipid or polymerized lipid, the method consisting of:

(a) selecting a cutinase enzyme;

(b) selecting a non-ionic surfactant or a combination of non-ionic surfactants compatible with said cutinase enzyme;

(c) forming an aqueous solution with a cleaning effective amount of said non-ionic surfactant or a combination of non-ionic surfactants and said enzyme wherein said concentration of said enzyme in said solution is at lease about 0.05 mg/liter;

(d) contacting the material with the solution of step (c); and (e) rinsing the material of step (d).

11. A method according to claim 10 wherein the cutinase is derived from *Pseudomonas mendocina*, ATCC 53552.

12. A method according to claim 11 wherein the cutinase is substantially free of other enzymes and enzyme sources.

13. A method according to claim 12 wherein the cutinase is isolated as a substantially pure microbially produced cutinase.

14. An improved method for enzymatically cleaning a material having a stain comprising a lipid or polymerized lipid, the method consisting of:

(a) selecting a cutinase enzyme;

(b) selecting a non-ionic surfactant or a combination of non-ionic surfactants compatible with said cutinase enzyme;

(c) forming an aqueous solution with a cleaning effective amount of said non-ionic surfactant or a combination of non-ionic surfactants and said enzyme wherein said concentration of said enzyme in said solution is at lease about 0.05 mg/liter;

(d) adding one or more enzymes selected from the group consisting of lipases, amylases, peroxidases and proteases to the aqueous solution;

(e) contacting the material with the solution of step (c); and (f) rinsing the material of step (e).

15. A method according to claim 10 wherein said cutinase is capable of causing hydrolysis of at least 10 percent by weight of a stain comprising a lipid or a polymerized lipid.

16. A method according to claim 10 wherein said cutinase is a non-naturally occurring cutinase having at least one amino acid randomly or selectively replaced by an amino acid not naturally found at that position.

* * * * *